United States Patent [19]

Dale

[11] Patent Number: 4,960,114
[45] Date of Patent: Oct. 2, 1990

[54] HAND SPLINT FOR STROKE PATIENTS

[76] Inventor: Charles L. Dale, 8666 111th St., N., Seminole, Fla. 34642

[21] Appl. No.: 419,992

[22] Filed: Oct. 11, 1989

[51] Int. Cl.⁵ ............................................. A61F 5/00
[52] U.S. Cl. ..................................... 128/87 R; 128/77
[58] Field of Search ...................... 128/77, 87 R, 87 A, 128/88, 89 R, 878, 879

[56] References Cited

U.S. PATENT DOCUMENTS

| | | | |
|---|---|---|---|
| D. 267,356 | 12/1982 | Kimzey | 128/89 R |
| 1,498,680 | 6/1924 | Clement | 128/77 |
| 3,724,456 | 4/1973 | Waxman | 128/877 |
| 3,776,225 | 12/1973 | Lonardo | 128/77 |
| 3,990,709 | 11/1976 | DeRogatis | 128/77 |
| 4,382,439 | 5/1983 | Shen | 128/77 |
| 4,441,490 | 4/1984 | Nirschl | 128/77 |
| 4,503,849 | 3/1985 | Morgan | 128/89 R |
| 4,666,158 | 5/1987 | Moro | 128/88 |
| 4,798,199 | 1/1989 | Hubbard | 128/87 R |
| 4,840,168 | 6/1989 | Lonardo | 128/77 |

Primary Examiner—Robert A. Hafer
Assistant Examiner—Michael Brown
Attorney, Agent, or Firm—Joseph C. Mason, Jr.; Ronald E. Smith

[57] ABSTRACT

A reversible hand splint having utility in connection with either the left or right hands of stroke patients. A generally cane handle-shaped, pear or egg-shaped base member is fixedly secured to the end of an elongate flat base-supporting member that is covered on both sides with a hook and loop type of fastening material. A cradle for a forearm has a complemental strip of the same type of fastening material so that the base member is easily inverted when the splint is changed from one hand to another. Elongate straps having their forwardmost ends secured to opposite ends of the egg-shaped base member are wrapped in crisscrossing relation to one another to retain the patient's forearm in the splint.

23 Claims, 12 Drawing Sheets

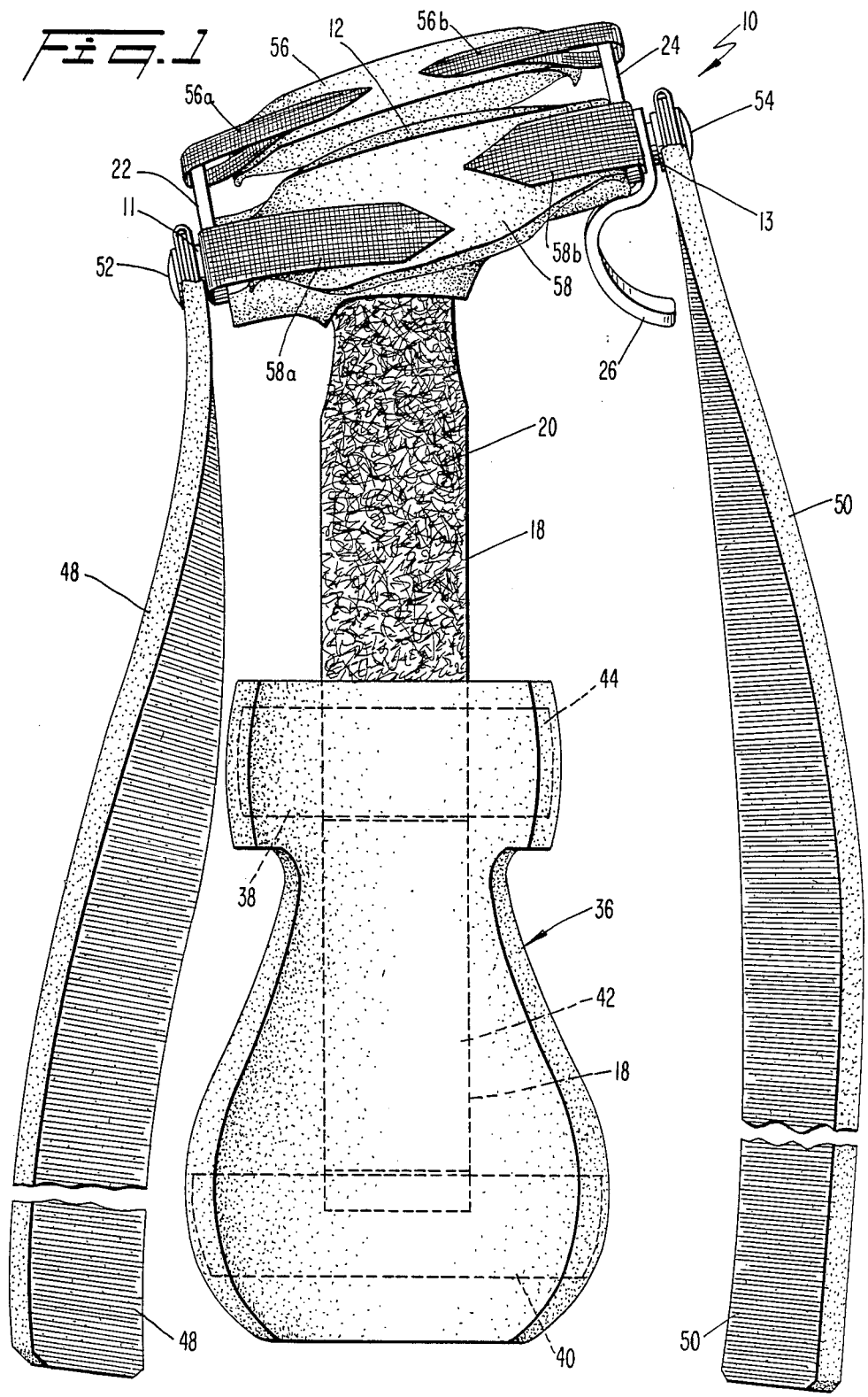

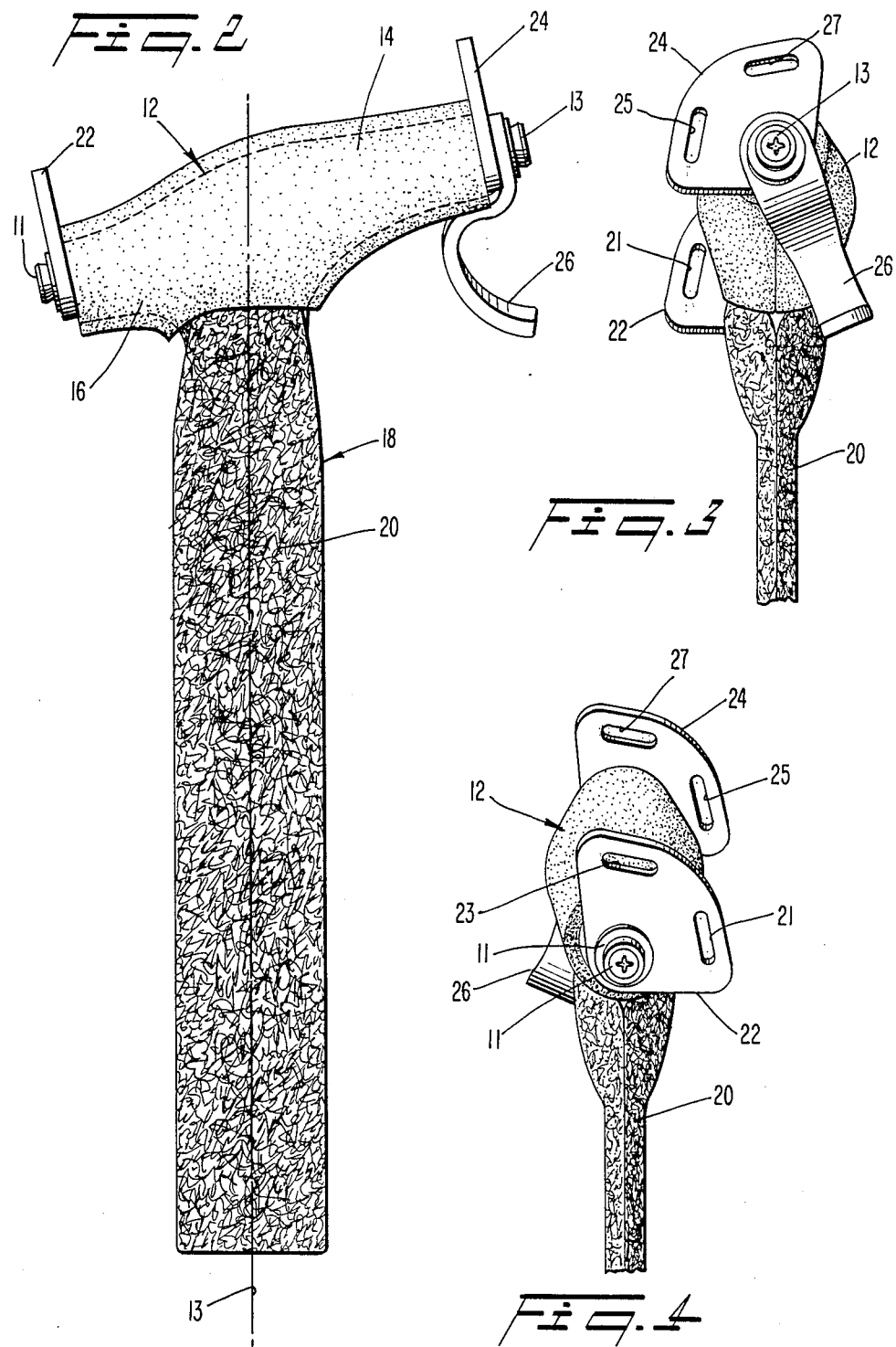

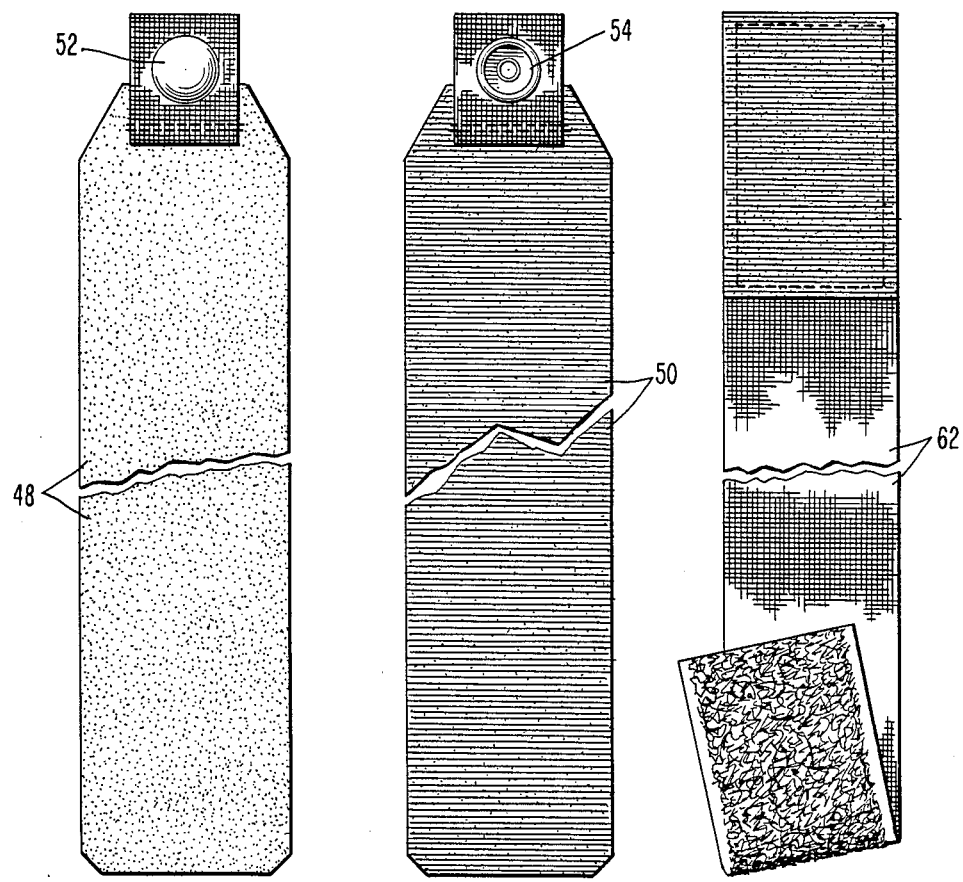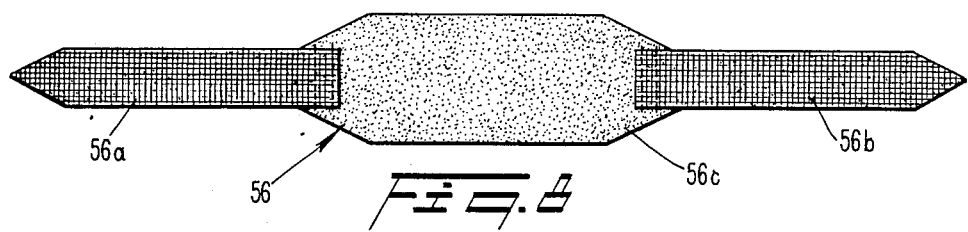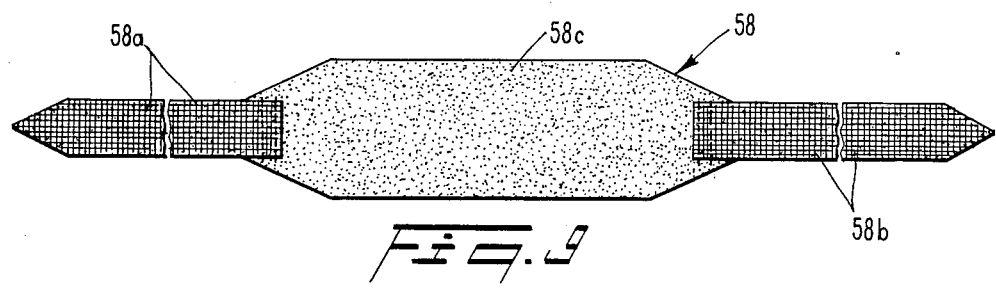

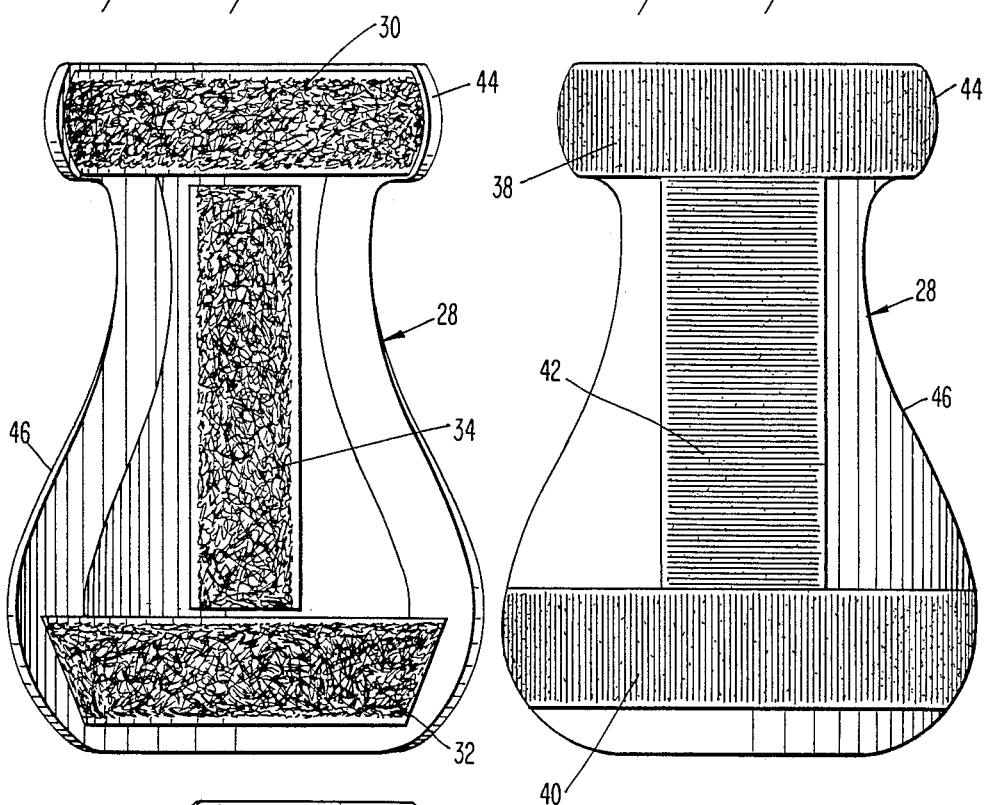
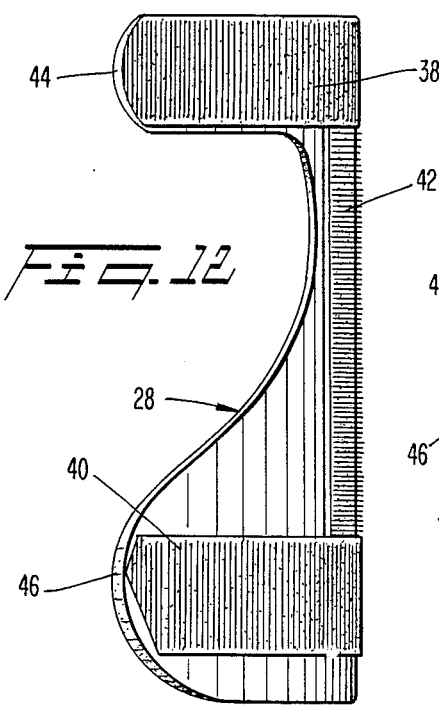
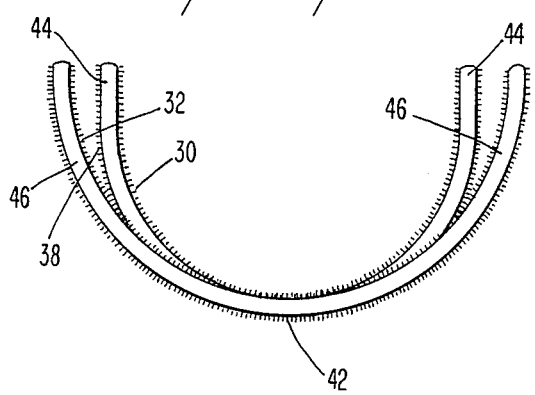

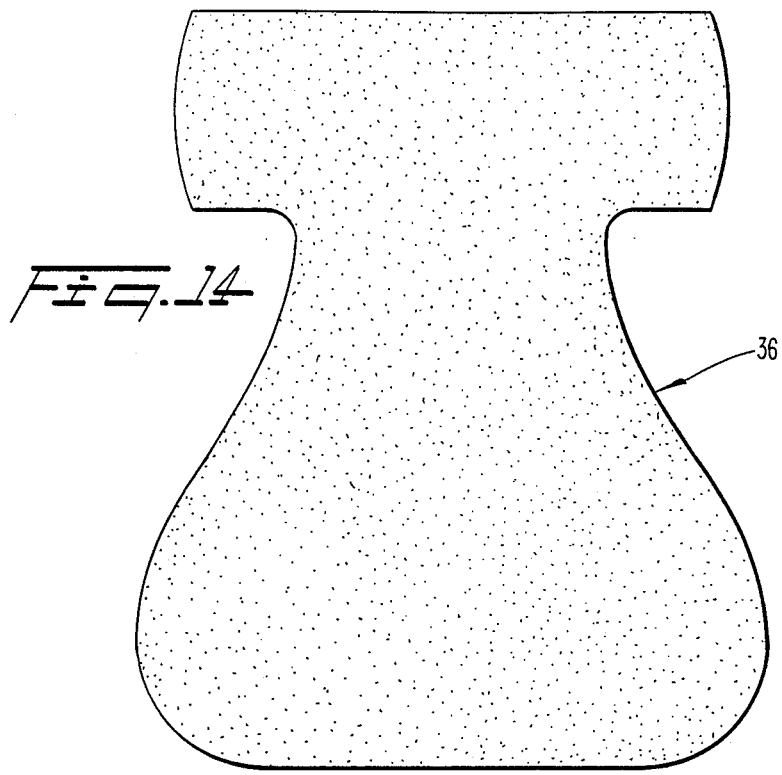
Fig. 14
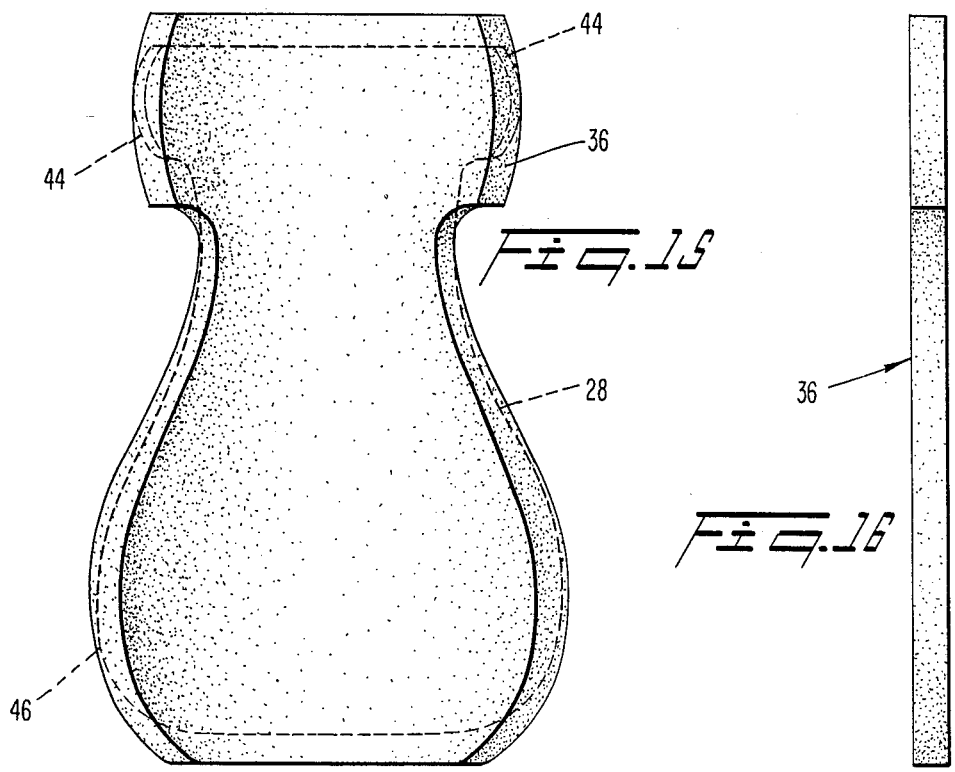
Fig. 15
Fig. 16

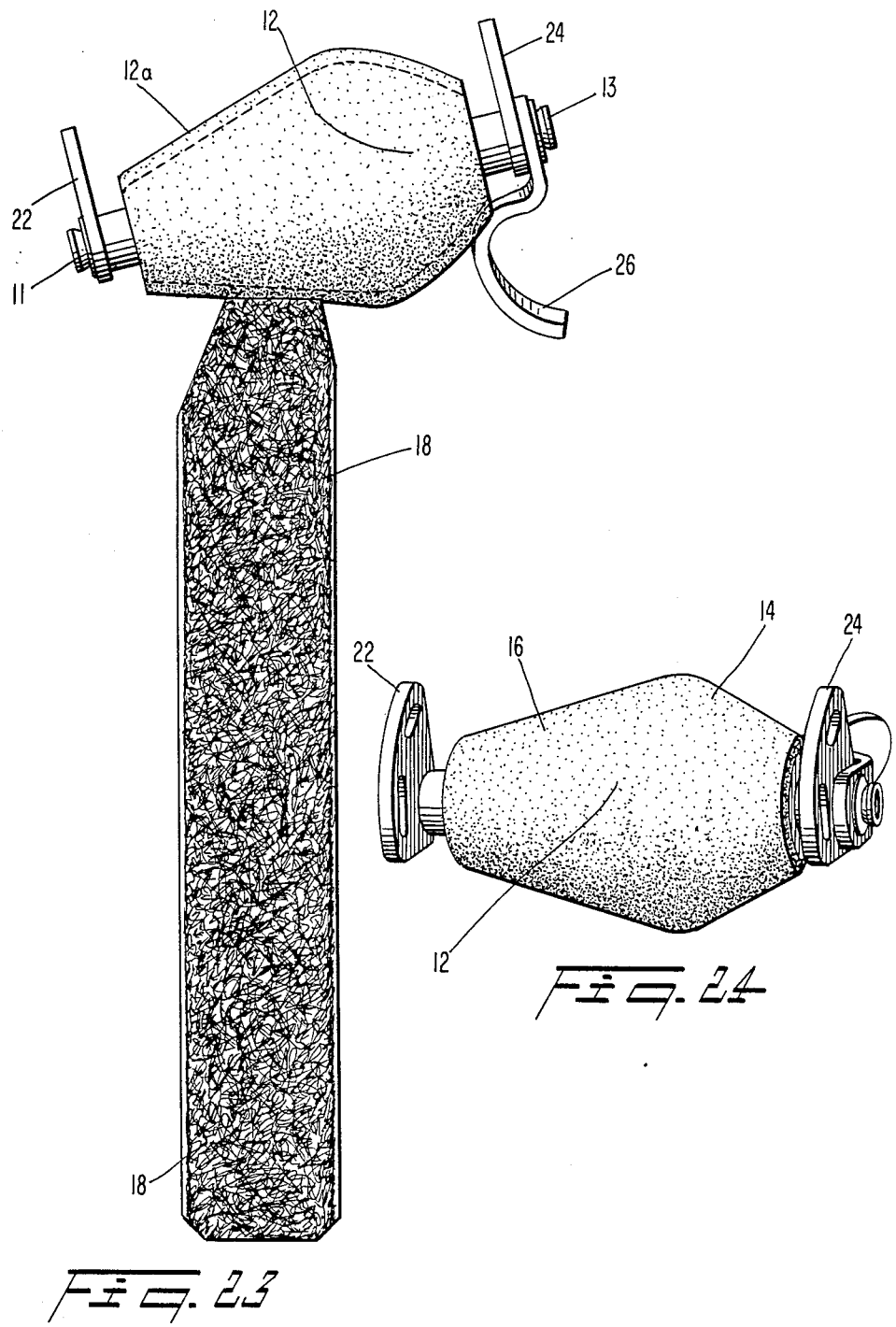

HAND SPLINT FOR STROKE PATIENTS

TECHNICAL FIELD

This invention relates, generally, to orthopedic devices such as splints. More particularly, it relates to a splint that maintains the hand of a stroke patient in a therapeutic position.

BACKGROUND ART

Stroke patients typically suffer a degree of paralysis on one side of the body; the paralysis can last a few days or for a lifetime, depending upon the severity of the stroke.

A hand of a stroke victim will often curl up upon itself, i.e., the thumb and fingers will close into a fist-like position. Moreover, the wrist will often turn down as well into a position known as a palmerflexion position.

Thus, there is a need for an orthopedic device that maintains a stroke patient's wrist and hand in a neutral position.

DISCLOSURE OF INVENTION

A stroke patient's hand is held in a therapeutic position by the novel device. The patient's thumb is abducted by an abductor member and the palm and fingers of the patient rest comfortably around a pear or egg shaped base member.

The base member is mounted at the end of a linear in configuration base supporting member which in turn is releasably secured to a cradle member that receives the patient's arm. The base member is inverted when used by a patient having a paralyzed left hand vis a vis its position when used by a patient having a paralyzed right hand.

The leading ends of elongate, flexible strap members are releasably secured to respective rotatably mounted mounting plates that are fixedly secured to opposite ends of the base member, and said strap members are helically wrapped about the patient's arm and said strap members the cradle part of the splint; advantageously, hook and loop fastening means are supplied on each side of the cradle member and the elongate straps are releasably held thereby.

Additional straps hold the patient's fingers in position around the base member.

It is therefore understood that the primary object of this invention is to provide a hand splint that maintains a stroke victim's hand in an optimal position.

A related object is to provide such a device that may be used for either the left hand or the right hand by simply inverting a part of the device.

Additional objects will become apparent as this description proceeds.

The invention accordingly comprises the features of construction, combination of elements and arrangement of parts that will be exemplified in the construction set forth hereinafter and the scope of the invention will be set forth in the claims.

DESCRIPTION OF THE DRAWINGS

For a fuller understanding of the nature and objects of the invention, reference should be made to the following detailed description, taken in connection with the accompanying drawings, in which:

FIG. 1 is a perspective view of a preferred embodiment of the device;

FIG. 2 is a top plan view of the base member of the device and its supporting member;

FIG. 3 is a side elevational view of the base member shown in FIG. 2;

FIG. 4 is a side elevational view taken from the opposite side of FIG. 3;

FIG. 5 is a plan view of one of the elongate strap members;

FIG. 6 is a plan view of the other elongate strap member;

FIG. 7 is a plan view of the wrist strap member of this invention;

FIG. 8 is a plan view of a finger retaining strap member;

FIG. 9 is a plan view of a knuckle retaining strap member;

FIG. 10 is a top plan view of the cradle member;

FIG. 11 is a bottom plan view of the cradle member;

FIG. 12 is a side elevational view of the cradle member;

FIG. 13 is an end view of the cradle member;

FIG. 14 is a top plan view of a pad member, in its flat configuration, that overlies the cradle member;

FIG. 15 is a top plan view showing the pad member of FIG. 14 disposed in its overlying relation to the cradle member;

FIG. 16 is a side elevational view of the pad member in its flat configuration;

FIG. 23 is a top plan view of an alternative embodiment of the base member; and

FIG. 24 is a perspective view of the alternative embodiment of the base member.

Similar reference numerals refer to similar parts throughout the several views of the drawings.

BEST MODES FOR CARRYING OUT THE INVENTION

Figure 17:
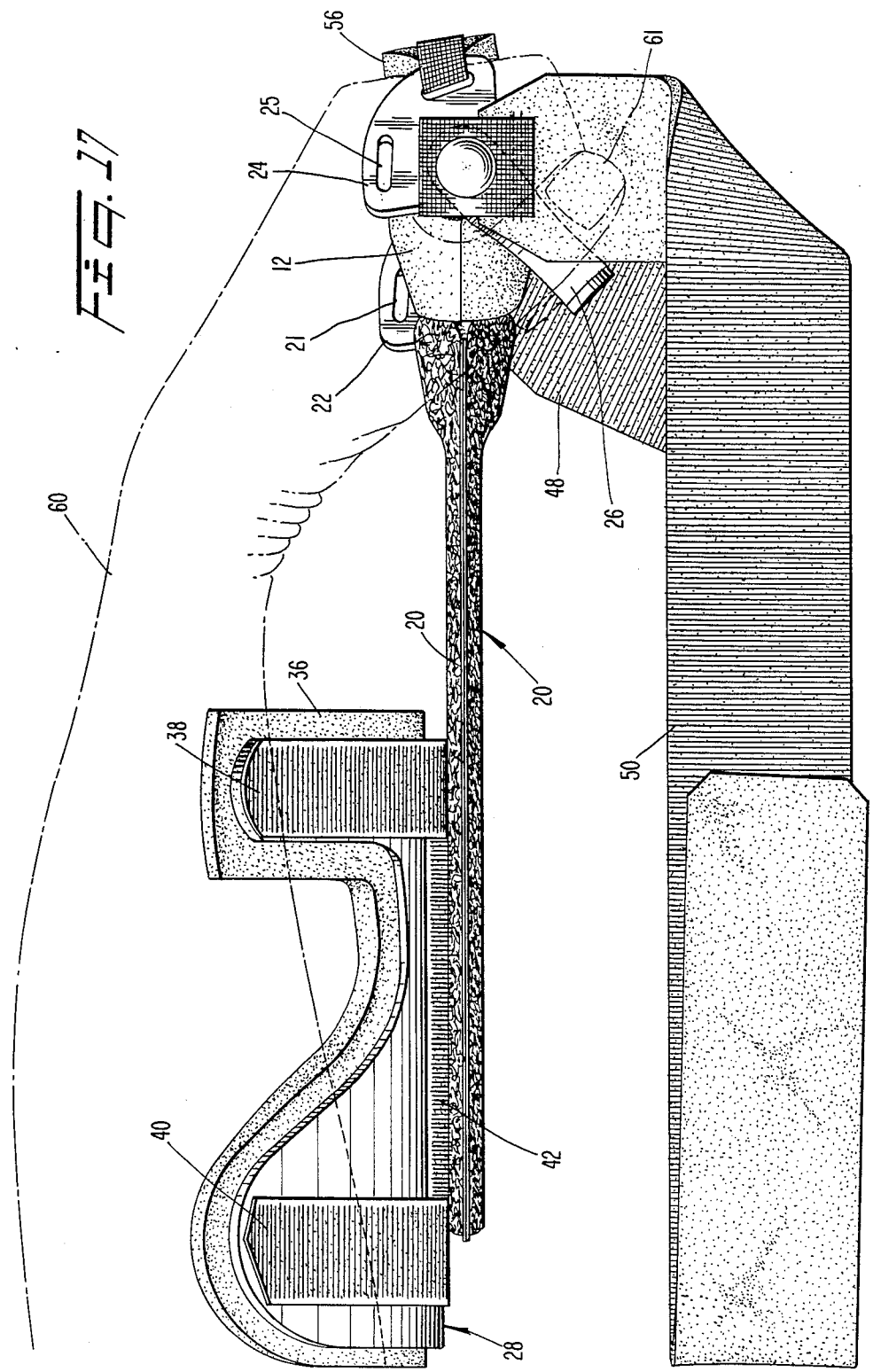
FIG. 17 is an elevational view of the novel apparatus when gripped by a patient's hand.

Referring now to FIG. 1, it will there be seen that an illustrative embodiment of the invention is denoted by the reference numeral 10 as a whole.

Rigid base member 12, in a preferred embodiment, has the unique configuration best seen in FIG. 2–4. Importantly, the configuration of base member 12 is such that it is suitable for grasping in the left hand of a stroke patient when in its FIG. 2 position and it is suitable for grasping by a right hand when inverted about longitudinal axis 13. The shape is similar to the shape of the handle of a cane.

Thus, the larger or more bulbous part 14 of base 12 is always grasped by the inner part of the patient's hand and the less bulbous part 16 thereof is grasped by the outer part of the patient's hand As used herein, "inner" refers to the thumb side of the hand and "outer" refers to the opposite side of the hand.

Base member 12 surmounts rigid supporting member 18 and is angled with respect thereto as shown, i.e., the longitudinal axis 15 of base 12 is disposed at a predetermined angle relative to the longitudinal axis 13 of the base supporting member 18. In a preferred embodiment, the angle is about twenty degrees. It should also be noted that base 12 is offset, with respect to axis 13 of member 18 i.e., the bulbous or thumb side of the base member 12 extends further from axis 13 than does the outer side of said member 12. Said base supporting member 18 is a flat, elongate member substantially covered by a layer of hook and loop fastening means 20 as shown.

Mounting plate 22 is rotatably mounted to the outer end of base member 12 by a buckle base member 11 and has two slots 21 and 23 formed therein. Mounting plate 24 is rotatably mounted to the inner side of base member 12 by a buckle base member 13 and has two slots 25, 27 formed therein.

A thumb abductor 26 overlies part of plate 24 as shown as is fixedly or rotatably secured thereto by said buckle base member 13. Importantly, buckle base members 11 and 13 extend through mounting plates 22, 24, respectively, and are anchored in the opposite ends of base 12.

As shown in FIG. 1, a cradle member 28 overlies and is releasably engaged to flat supporting member 18. Importantly, cradle 28 may be placed in different positions along the extent of supporting member 18. Thus, hand splint 10 can easily accommodate arms of differing lengths.

Cradle member 28 is best shown in FIGS. 10-13. In FIG. 10, a pair of top side transverse strips of hook and loop material are denoted 30, 32, and a top side longitudinal strip of such material disposed in interconnecting relation therebetween is denoted 34. These strips of material may be riveted or glued into position. A foam pad member 36, shown in FIGS. 14-16, overlies strips 30, 32 and 34 of cradle member 28, as shown in FIGS. 1 and 15, to cushion the patient's arm when device 10 is in use.

Returning to FIGS. 10-13, it will be seen in FIG. 11 that three strips of hook and loop material, denoted 38, 40 and 42 are fixedly secured to the bottom side of cradle member 28. Strip 42 releasably engages the hook and loop material 20 that covers support member 18 when cradle 28 is releasably secured to member 18 as depicted in FIG. 1. These strips of material may also be secured into position by rivets, adhesive, or the like.

Cradle 28 includes forward and rearward transverse arm guide members 44, 46, the construction of which is best understood in connection with FIGS. 10-13, and specifically FIG. 13.

Reference can now again be made to FIG. 1.

A pair of flexible, elongate strip members 48, 50 are releasably secured to opposite sides of base member 12 as shown. Specifically, each strap carries a buckle means 52, 54 at its leading end and said buckles 52, 54 snap fittingly engage the buckle base members, 11 and 13, that were pointed out in connection with FIG. 2.

FIG. 1 also depicts auxiliary strap members 56 and 58 which are slidably received within the slots formed in rotatably mounted mounting plate members 22, 24. Opposite ends of strap 56 extend through slots 23 and 27 of plates 22 and 24, respectively, and the opposite ends of strap 58 extend through slots 21, 25 of plates 22, 24, respectively. These straps 56, 58 are shown in their unfolded configuration in FIGS. 8 and 9, respectively. The opposite ends 56a, 56b of strap 56 releasably engage medial part 56c thereof as all parts are suitable covered with a hook and loop material; strap 58 has a similar construction as indicated by the similar reference numerals in FIG. 9. The opposite ends of each strap 56, 58 overlie the respective medial parts when said straps are operatively disposed over a patient's hand as will be shown hereinafter and as shown in FIG. 1 when the splint is not in use.

To secure hand splint 10 to a patient's arm, the affected arm 60 is cradled within pad 36 that overlies cradle member 28 as depicted in FIG. 17 and the patient's hand is placed around base member 12. Strap 56 may be placed in overlying relation to the patient's fingers at this time, as shown. However, strap member 56 may be placed into a different position by simply pivoting mounting plate members 22, 24 about their respective pivot points, i.e., about the center of the buckle base members 11 and 13, respectively. The thumb 61 is abducted by abductor member 26 as shown. The hand of the patient is shown in a typical palmerflexion position in FIG. 17.

Figure 18:
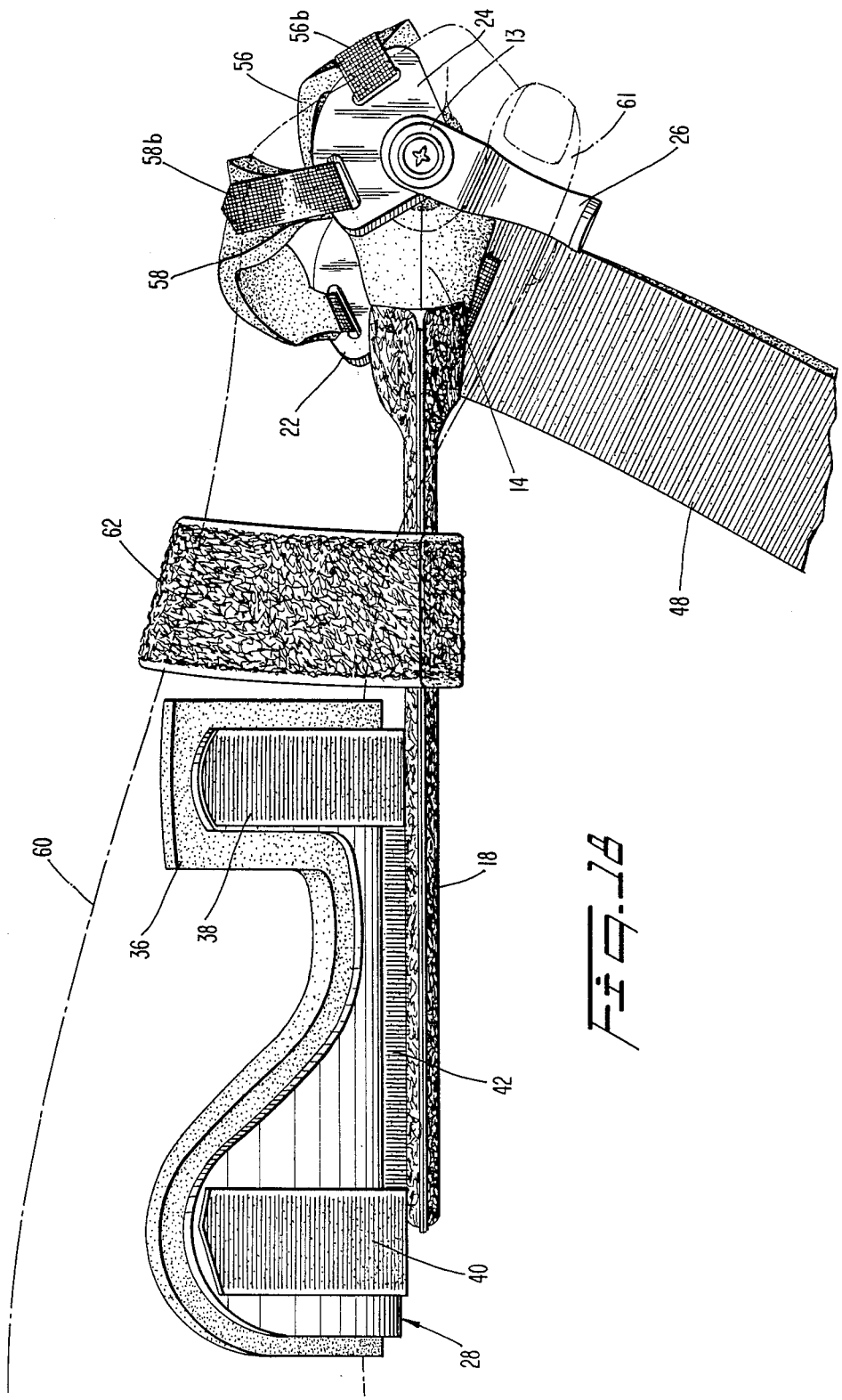
FIG. 18 is a view similar to that of FIG. 17, but showing the wrist strap of FIG. 7 wrapped about the patient's wrist and the supporting member to hold the patient's arm in the cradle member.

As shown in FIG. 18, a wrist strap member 62 (also shown in FIG. 7) is placed over the patient's wrist and under support member 18 to pull the patient's wrist down into cradle 28. Wrist strap 62 is suitably covered with hook and loop material to facilitate its attachment. Strap member 58 may be secured in overlying relation to the patient's metacarpophalangeal joints at this time, as depicted. However, strap member 58 may be placed into a different position by simply pivoting mounting plate members 22, 24 about their respective pivot points, i.e., about the center of the buckle base members 11 and 13, respectively.

Figure 19:
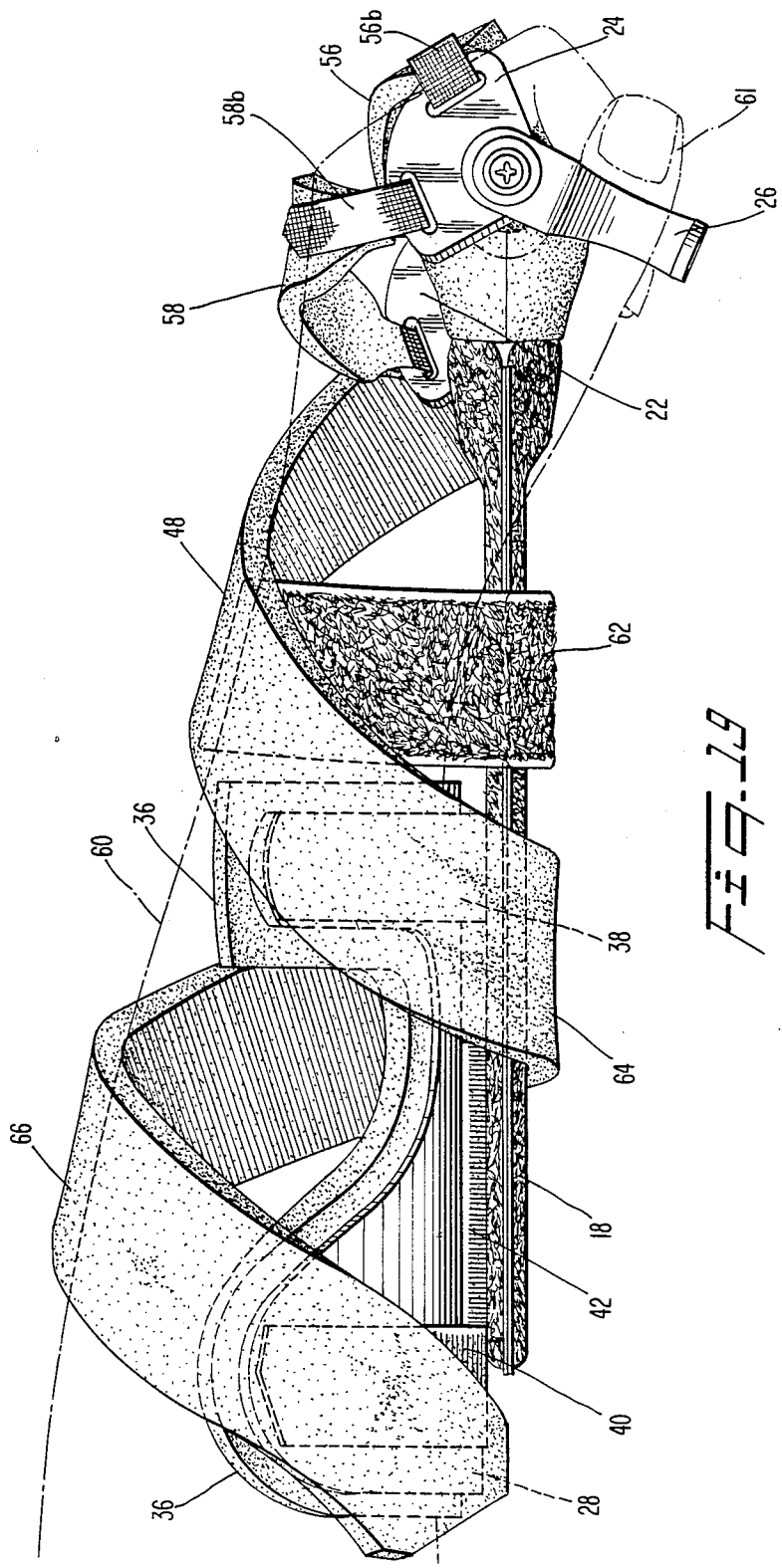
FIG. 19 is similar to FIG. 18, but shows one of the elongate strap members disposed in helical disposition around the patient's arm and in releasable engagement with longitudinally spaced parts of the cradle member.

As shown in FIG. 19, strap member 48 is then crossed over the patient's wrist and wrist strap 62 and over hook and loop member 38 on the underside of arm 44 of cradle 28, under the base supporting member 18 as at 64, over the patient's arm a second time as at 66 and the free end of said strap member 48 is then releasably secured to rearward hook and loop member 40 of cradle 28 as shown.

Figure 20:
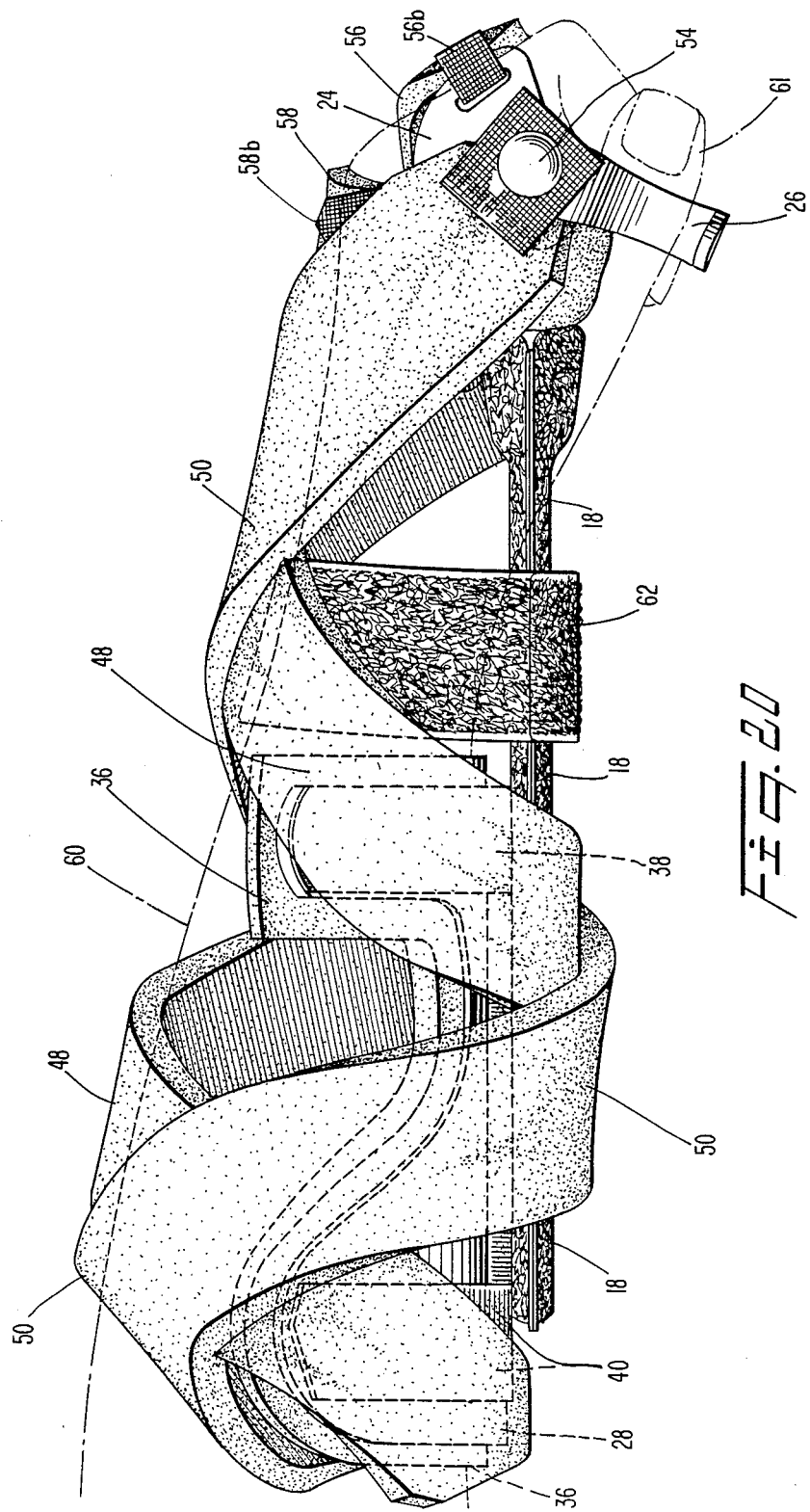
FIG. 20 is a view similar to FIG. 19, but showing the other elongate strap member also helically disposed about the arm in a reverse direction.

Next, as shown in FIG. 20, strap member 50 is helically wrapped about the patient's arm in a reverse manner, i.e., it is crossed over the patient's wrist, over forward hook and loop member 38, under base member 18, and back over the patient's arm a second time into releasable engagement with rearward hook and loop member 40 of cradle member 28.

Figure 21:
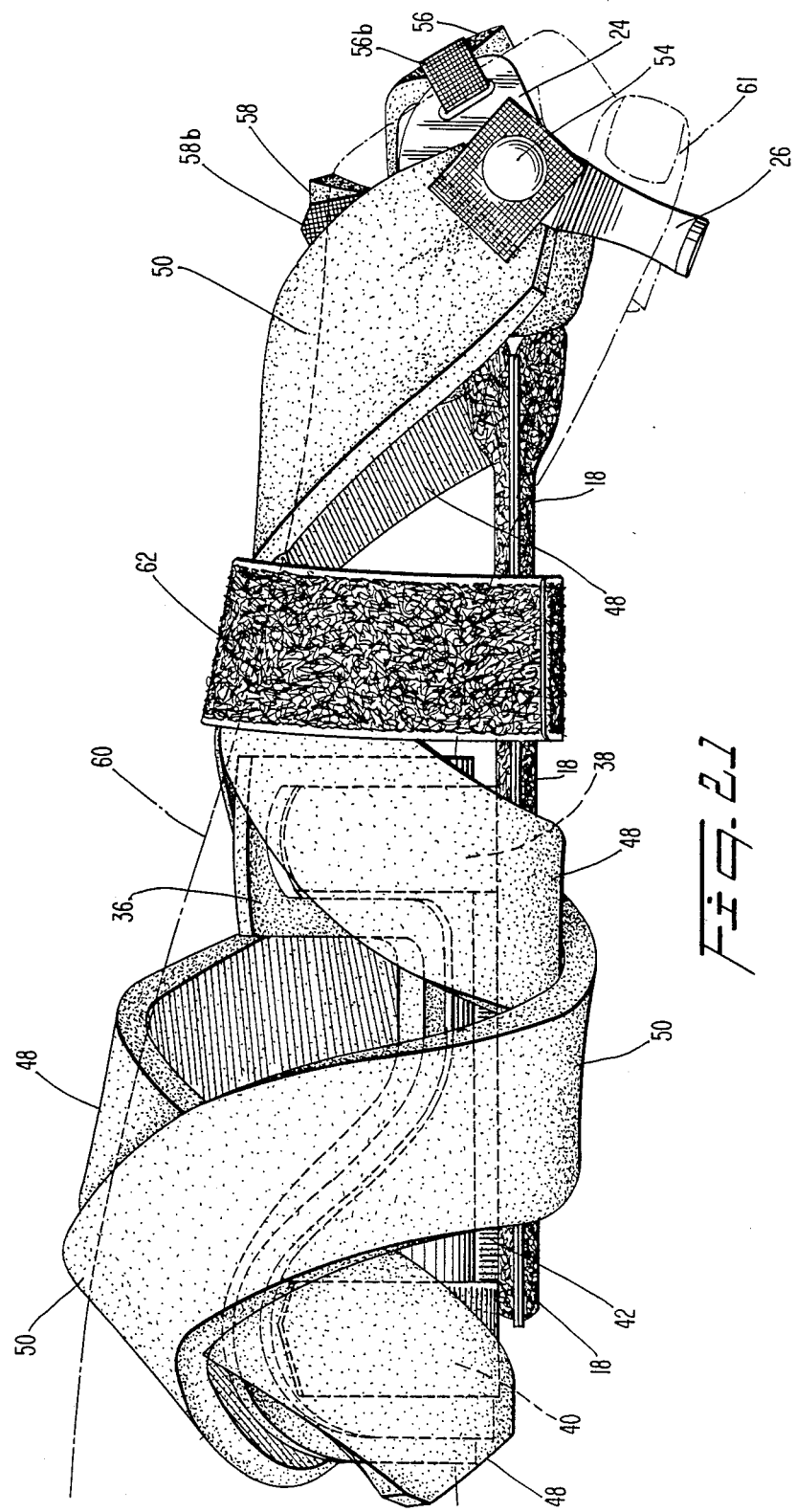
FIG. 21 is a view similar to that of FIG. 20, but showing the wrist strap member removed from the patient's wrist and disposed on the outside of the elongate strap members.

Strap 62 can then be pulled out from under straps 48, 50 and placed into its FIG. 21 position, overlying said straps as shown to hold the patient's wrist down as desired.

Figure 22:
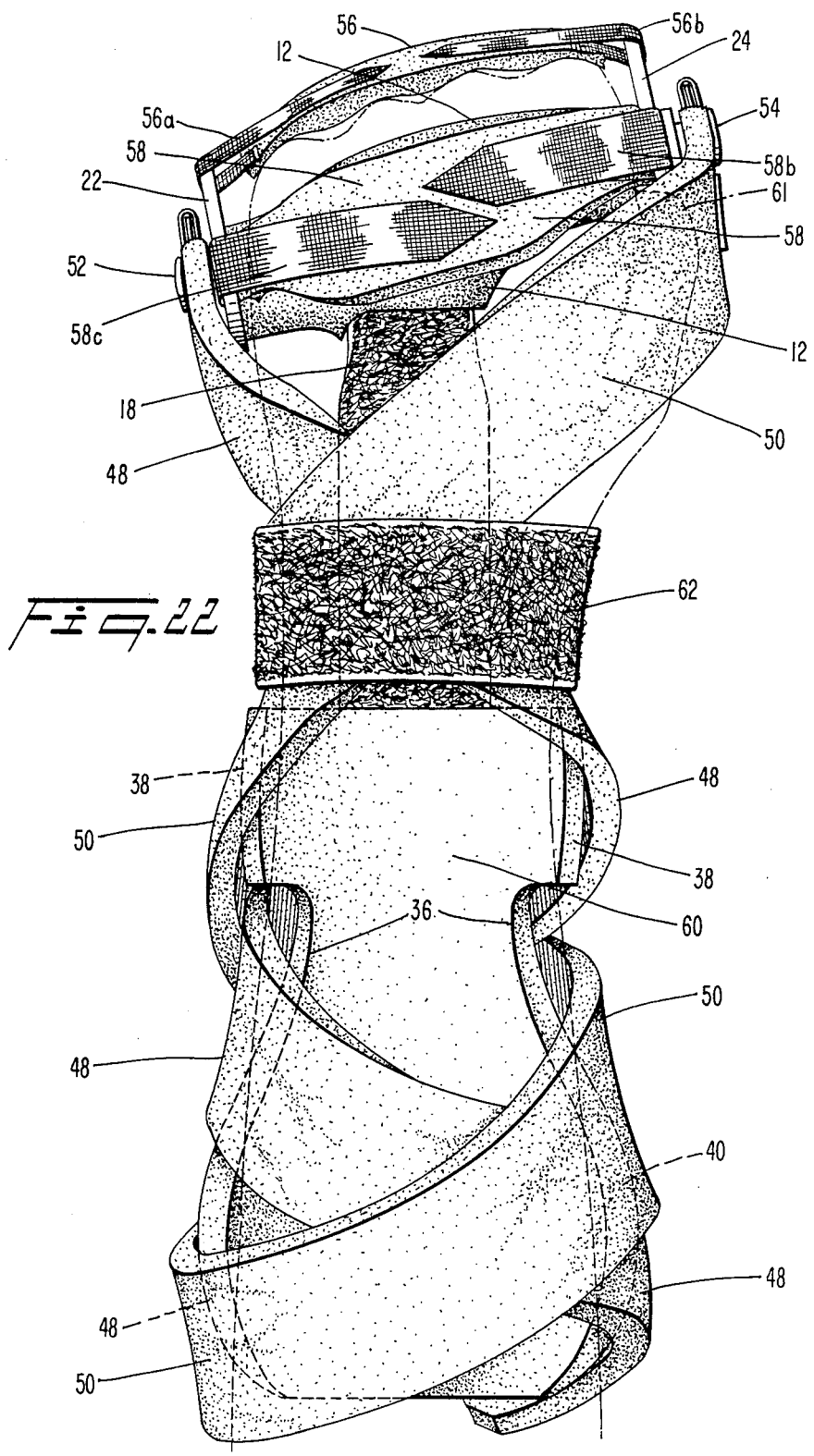
FIG. 22 is a top plan view of the parts shown in FIG. 21.

The reverse helical wrapping of the strap members 48, 50 is perhaps best understood in connection with FIG. 22.

An alternative embodiment of the base member is shown in FIGS. 23 and 24. The reference numerals are the same as in the other embodiments because only the shape of the base member 12 is different. Also, base member 12 can be covered with a pad 12a to effectively increase the size of base member 12 and to provide increased upward flex to the patient's wrist. The alternative base member is shown in its uncovered configuration in FIG. 24. This larger, pear or egg-shaped base member may have greater utility in connection with patient's having large hands. However, it is very similar to the first-described base member in that its most bulbous part 14 is positioned toward the inner part of the patient's hand, and its less bulbous part 16 is positioned toward the outer part of the patient's hand. Base member 12 is also angled with respect to base supporting member 18 as shown in FIG. 23.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A hand splint comprising:
   a base member;
   said base member being configured to support a human hand in a slightly open fist position;
   an elongate, rigid base supporting member of flat, lineal configuration;
   said rigid base supporting member having a first side and a second side;
   said rigid base supporting member having a first, leading end and a second, trailing end longitudinally spaced therefrom;
   said base member being fixedly secured to said first end of said base supporting member;
   a cradle member for cradling the forearm of a stroke patient;
   a hook and loop fastening means being fixedly secured to a bottom side of said cradle member;
   at least a first side of said rigid base supporting member being covered by a second hook and loop fastening means complemental to said first hook and loop fastening means so that at least a first side of said rigid base supporting member is releasably securable to the bottom side of said cradle member and
   means circumscribing a patient's wrist and said base supporting member to hold the patient's forearm wholly within said cradle member.

2. The splint of claim 1, wherein said base member has a first bulbous part and an integral second part of reduced diameter.

3. The splint of claim 2, wherein said base member has a longitudinal axis of symmetry disposed at a predetermined angle relative to a longitudinal axis of symmetry of said base supporting member.

4. The splint of claim 3, wherein said predetermined angle is about ten degrees.

5. The splint of claim 3, further comprising a hook and loop fastener material disposed in overlying relation to said first and second sides of said rigid base supporting member;
   whereby inverting said base support member relative to said cradle member enables grasping of said base member by either a left or right hand.

6. The splint of claim 5, wherein said cradle member has a top side and a bottom side, and wherein a hook and loop fastener material complemental to the hook and loop material covering both sides of said base supporting member is secured to said cradle member bottom side;
   said cradle member being releasably securable to either side of said base supporting member at any preselected point along the extent of said base supporting member;
   whereby the splint accommodates forearms of differing lengths and whereby the base member is reversibly mounted with respect to said cradle member so that said base member is graspable by either a left hand or a right hand.

7. The splint of claim 6, further comprising a first transversely disposed strip of hook and loop fastening material fixedly secured to the bottom side of said cradle member at a leading end thereof and a second transversely disposed strip of hook and loop fastening material fixedly secured to the bottom side of said cradle member at a trailing end thereof.

8. The splint of claim 7, wherein said base member has flat opposite ends and wherein a first and second flat mounting plate member is rotatably secured to each of said ends, said first plate member being disposed on an outer end of said base member and said second plate member being disposed on an inner end of said base member.

9. The splint of claim 8, further comprising a thumb abductor member secured to said inner end of said base member in overlying relation to said second plate member.

10. The splint of claim 9, wherein said first and second plate members and said abductor member are rotatably secured to their respective ends of said base member by first and second buckle base members that extend through said parts secured thereby and into said base member to mount said parts to said base member and said buckle base members further providing a base means to which first and second buckle members are releasably attachable.

11. The splint of claim 10, further comprising a pair of first and second elongate strap members;
    each of said strap members having a leading end and a trailing end;
    said first strap member carrying a first buckle member at its leading end;
    said second strap member carrying a second buckle member at its leading end;
    said first buckle member releasably engaging said first buckle base member; and
    said second buckle member releasably engaging said second buckle base member so that said first and second strap members are releasably secured at their respective leading ends to said outer and inner sides of said base member, respectively.

12. The splint of claim 11, wherein said strap members have a common length, and wherein said common length is greater than the extent of said base supporting member.

13. The splint of claim 11, wherein said first strap member is wrapped helically about a patient's forearm resting in said cradle member, and wherein longitudinally spaced parts of said first strap member releasably engage said first and second transversely disposed strips of hook and loop fastening material secured to the bottom side of said cradle member.

14. The splint of claim 13, wherein said parts of said first strap member engage said strips at an inner end of said strips.

15. The splint of claim 13, wherein said second strap member is wrapped helically about a patient's forearm resting in said cradle member, and wherein longitudinally spaced parts of said second strap member releasably engage said first and second transversely disposed strips of hook and loop fastening material secured to the bottom side of said cradle member.

16. The splint of claim 15, wherein said parts of said second strap member engage said strips at an outer end of said strips.

17. The splint of claim 15, further comprising a transversely disposed wrist strap member disposed in overlying relation to a wrist of a patient, said wrist strap member circumscribing said wrist and said base supporting member to hold said wrist down so that the patient's forearm is fully received within said cradle member before said first and second straps are helically wrapped therearound.

18. The splint of claim 15, wherein said a transversely disposed wrist strap member is disposed in circumscribing relation to said first and second helically wrapped strap members and said base supporting member in the region of the patient's wrist to hold the patient's forearm fully within said cradle member.

19. The splint of claim 15, wherein said first and second mounting plate members are cooperatively slotted and wherein a first hand strap member has its opposite ends secured to transversely disposed, cooperatively positioned slots formed in said mounting plate members, said first hand strap member being disposed in overlying relation to a preselected part of the patient's hand to maintain said hand in its proper position relative to said base member.

20. The splint of claim 19, further comprising a second hand strap member having its opposite ends secured to transversely disposed, cooperatively positioned slots formed in said mounting plate members;
   said second hand strap member being disposed in overlying relation to a preselected part of a patient's hand to maintain said hand in its proper position relative to said base member.

21. The splint of claim 1, further comprising a resilient, soft pad member disposed in overlying relation to a top side of said cradle member, and further comprising means releasably securing said pad member to said cradle member.

22. The splint of claim 1, wherein said base member is offset with respect to a longitudinal axis of said base supporting member, an inner end of said base member extending transversely further from said longitudinal axis than an outer end of said base member.

23. The splint of claim 1, further comprising a soft pad member disposed in overlying relation to said base member to increase the effective size of said base member to accommodate larger hands and to provide enhanced comfort to the patient's hand.

* * * * *